United States Patent [19]

Yost et al.

[11] Patent Number: 5,736,642
[45] Date of Patent: Apr. 7, 1998

[54] NONLINEAR ULTRASONIC SCANNING TO DETECT MATERIAL DEFECTS

[75] Inventors: William T. Yost, Newport News; John H. Cantrell, Yorktown, both of Va.

[73] Assignee: The United States of America as represented by the Administrator of the National Aeronautics and Space Administration, Washington, D.C.

[21] Appl. No.: 778,066

[22] Filed: Jan. 8, 1997

[51] Int. Cl.⁶ .......................... G01N 29/06; G01N 29/26
[52] U.S. Cl. .................. 73/602; 73/625; 73/628; 73/641; 128/660.07; 128/660.09; 128/661.01
[58] Field of Search ........................ 73/602, 606, 620, 73/622, 625, 626, 627, 628, 641; 128/661.01, 660.01, 660.07, 660.09; 364/550; 367/103

[56] References Cited

U.S. PATENT DOCUMENTS

| | | | |
|---|---|---|---|
| 3,693,415 | 9/1972 | Whittington | 73/622 |
| 4,275,598 | 6/1981 | Engl | 73/622 |
| 4,435,984 | 3/1984 | Gruber | 73/628 |
| 4,528,853 | 7/1985 | Lerch et al. | 73/624 |
| 4,566,333 | 1/1986 | Chubachi et al. | 73/642 |
| 5,189,915 | 3/1993 | Reinhart et al. | 73/623 |
| 5,211,059 | 5/1993 | Hayakawa et al. | 73/606 |
| 5,253,276 | 10/1993 | Mortenson et al. | 376/249 |
| 5,280,724 | 1/1994 | Higo et al. | 73/624 |
| 5,341,683 | 8/1994 | Searle | 73/597 |
| 5,349,862 | 9/1994 | Chubachi et al. | 73/602 |
| 5,402,681 | 4/1995 | Nakaso et al. | 73/602 |
| 5,408,882 | 4/1995 | McKinley et al. | 73/597 |

*Primary Examiner*—Hezron E. Williams
*Assistant Examiner*—Rose M. Miller
*Attorney, Agent, or Firm*—Kimberly A. Chasteen

[57] ABSTRACT

A method and system are provided to detect defects in a material. Waves of known frequency(ies) are mixed at an interaction zone in the material. As a result, at least one of a difference wave and a sum wave are generated in the interaction zone. The difference wave occurs at a difference frequency and the sum wave occurs at a sum frequency. The amplitude of at least one nonlinear signal based on the sum and/or difference waves is then measured. The nonlinear signal is defined as the amplitude of one of the difference wave and sum wave relative to the product of the amplitude of the surface waves. The amplitude of the nonlinear signal is an indication of defects (e.g., dislocation dipole density) in the interaction zone.

20 Claims, 5 Drawing Sheets

5,736,642

1

NONLINEAR ULTRASONIC SCANNING TO DETECT MATERIAL DEFECTS

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

This invention relates to detecting material defects. More specifically, the invention is a method and system of detecting dislocations and defects in a material caused by fatigue, heat treatment anomalies or other consequences of process and use.

2. Description of the Related Art

During the life of a structure, material defects are manifested in stages. Initially, heat treatment anomalies and dislocations are often residuals of the various manufacturing processes. During service life, fatigue brought on by cyclic loading of a structure promotes the formation of additional dislocations which are at first isolated (monopoles). Eventually, the dislocation monopoles form dislocation dipoles as the trapped dislocations move back and forth in response to cyclic stresses. As the dislocations grow into networks, additional voids in the structure are formed. Over time, the voids coalesce into cracks which propagate throughout the structure. The final stage is failure once the cracks have grown large enough.

Current methods and apparatus exist for detecting and/or locating cracks of various sizes. However, if the earlier stages of fatigue (e.g., dislocations) can be detected, a structure's susceptibility to crack formation and failure could be predicted. In this way, a structure could be repaired or taken out of service before there was any danger of structural failure.

SUMMARY OF THE INVENTION

Accordingly, it is an object of the present invention to provide a method and system for detecting the early stages of fatigue or other service life induced defects in a structure.

Another object of the present invention is to provide a method and system for examining a structure from easily accessible vantage points to detect the early stages of fatigue or other service life induced defects.

Other objects and advantages of the present invention will become more obvious hereinafter in the specification and drawings.

In accordance with the present invention, a method and system are provided to detect defects in a material. Waves of a first frequency are mixed with waves of a second frequency at an interaction zone in the material. The first and second frequencies can be the same or different. As a result, at least one of a difference wave and a sum wave are generated in the interaction zone. The difference wave occurs at the first frequency minus the second frequency and the sum wave occurs at the first frequency plus the second frequency. The amplitude of at least one nonlinear signal is then measured. The nonlinear signal is defined as the amplitude of one of the difference wave and sum wave relative to the product of the amplitude of the surface waves of the first frequency and the amplitude of the surface waves of the second frequency. The amplitude of the nonlinear signal is an indication of defects (e.g., dislocation dipole density) in the interaction zone.

DETAILED DESCRIPTION OF THE INVENTION

Figure 1:
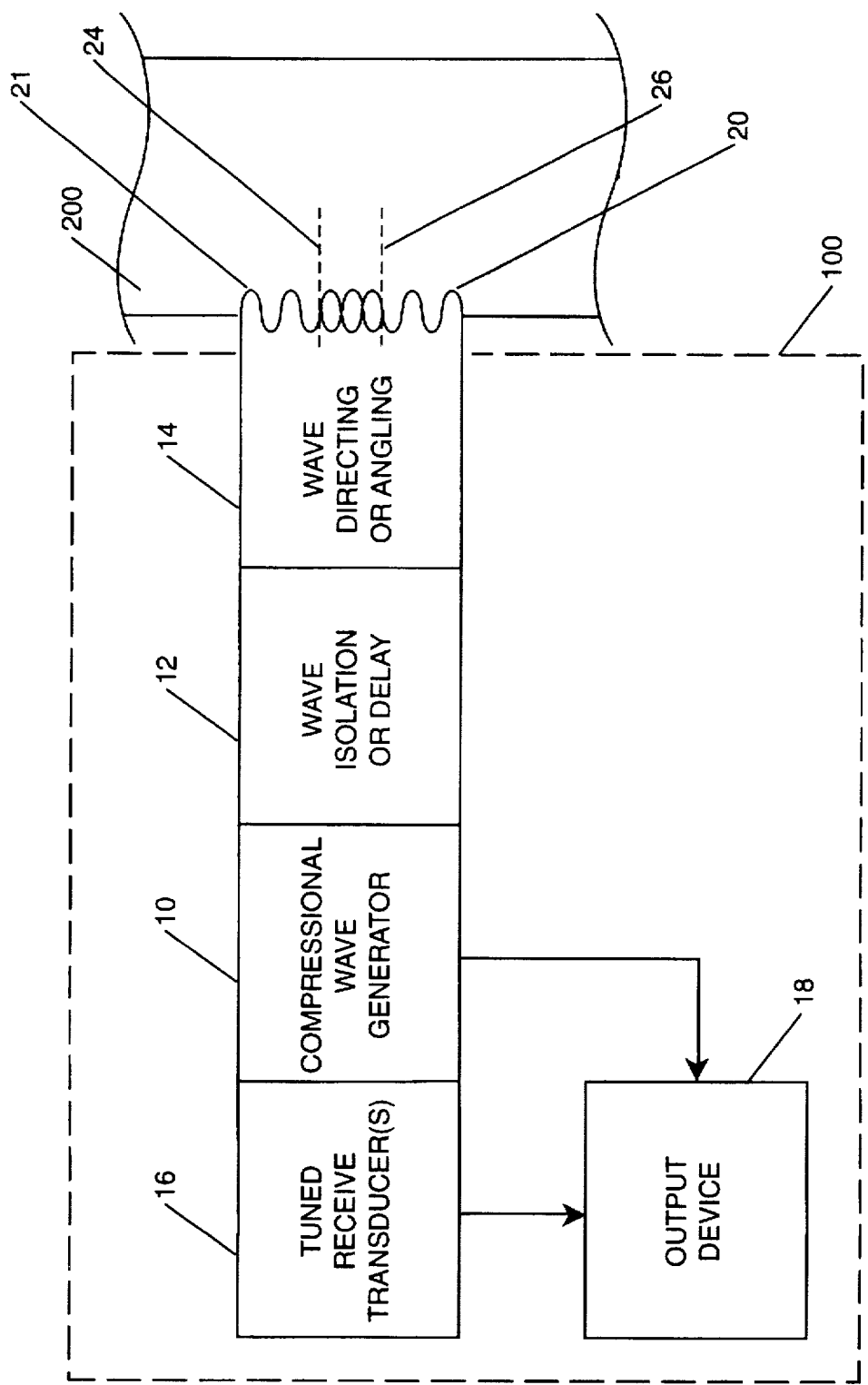
FIG. 1 is a block diagram of an embodiment of a scanning system for detecting the early stages of fatigue or other service life induced defects in a material or structure in accordance with the present invention.

Referring now to the drawings, and more particularly to FIG. 1, a block diagram of a material scanning system according to one embodiment of the present invention is shown and confined within the dashed line box referenced by numeral 100. System 100 implements a simple and novel method for detecting dislocation dipoles in a material or structure under test 200. Because the present invention relies on acoustic transmission and reception, blocks 10, 12, 14 and 16 are shown connected to one another and material 200 to indicate good ultrasonic coupling therebetween. While particular embodiments of system 100 will be presented below, scanning system 100 could be realized in a variety of ways as will be understood by one of ordinary skill in the art.

It has previously been shown that dislocation dipoles significantly contribute to the generation of (nonlinear) second order harmonics. The dislocation dipole contribution to the nonlinearity can be substantial when compared to the anharmonicity of the material's crystalline lattice. This is especially true when the dipole density is large. See "Acoustic Harmonic Generation From Fatigue-induced Dislocation Dipoles," by Cantrell and Yost, Philosophical Magazine, Volume 69, No., 2, pp. 315-326, 1994. The present invention presents a simple method and system of detecting the dislocation dipoles of a material or structure before they develop into voids and grow to form cracks.

System 100 uses compressional wave generation block 10 to generate first and second compressional waves of the same or differing frequency. For the purpose of the illustrated example, it will be assumed that the first and second compressional waves are different frequencies. In the preferred configuration, both waves are pulsed so that measurements can be made when generator block 10 is off for ease of interpretation of results. Both waves are in the ultrasonic frequency range above approximately 500 kHz to achieve a high degree of wave mixing necessary in the present invention. Both waves are generated simultaneously or with some degree of overlap for reasons that will become clearer below. Coupled to generator block 10 is a wave isolation or delay block used to isolate each of the generated compressional waves from the (source) generator block 10. Whether by means of isolation or delay, the function of block 12 is to prevent any reflection of the compressional waves from material 200 back to generator block 10 during the time of amplitude measurement. This prevents interference with the source signals during measurement.

In wave directing or angling block 14, the two compressional waves so isolated (or delayed) are directed to material 200. At least a portion of the compressional waves can be directed towards one another to form surface waves 20 and 21 at material 200 that at least partially penetrate into material 200. Surface waves 20 and 21 interact most strongly with one another in a region or zone of interaction designated in the drawings by the zone residing between dashed lines 24 and 26. As a result of such interaction, a sum wave and a difference wave are generated. The sum wave occurs at a frequency equal to the first frequency plus the second frequency. The difference wave occurs at a frequency equal to the first frequency minus the second frequency. When the wave interaction occurring between lines 24 and 26 is scanned across material 200 and encounters a zone of damage (e.g., dislocation dipole brought on by fatigue, a heat treatment anomaly, etc.), a nonlinear signal defined by $$\frac{A_{(f_1 \neq f_2)}}{A_{f_1} \cdot A_{f_2}} \quad (1)$$

experiences a large increase in value. This is because dislocations influence the generation of harmonics if the dislocations are in a dipole configuration. In equation (1), $A_{f_1}$ is the amplitude of surface wave 20 at the first frequency, $A_{f_2}$ is the amplitude of surface wave 21 at the second frequency. $A_{(f_1+f_2)}$ is the amplitude of the sum wave at a frequency $(f_1+f_2)$ resulting from the wave interaction occurring between lines 24 and 26, and $A_{(f_1-f_2)}$ is the amplitude of the difference wave at a frequency $(f_1-f_2)$ resulting from the wave interaction occurring between lines 24 and 26.

During the scanning of material 200, the amplitude signals used by equation (1) are continuously monitored. Monitoring can be accomplished by measuring each amplitude in equation (1). However, it is also possible to only measure the amplitude of the sum ($A_{(f_1+f_2)}$) and/or difference ($A_{(f_1-f_2)}$) waves as an indication of nonlinearity if the source amplitudes ($A_{f_1}$ and $A_{f_2}$) are each held fixed.

In the configuration of FIG. 1, monitoring occurs from the side of material 200 from which the compressional waves were generated. This has the advantage of allowing all of system 100 to be arranged on one side of material 200. This is especially useful when scanning an existing structure (e.g., aircraft, building, etc.) to which two-sided access is difficult or impossible to achieve. In general, the nonlinear signal(s) are monitored by a transducer(s) tuned to the particular sum or difference frequency associated with the corresponding sum or difference signal. For example, if $f_1$ is 31 MHz and $f_2$ is 30 MHz, tuned receive transducer(s) block 16 can be implemented by a single transducer tuned to 61 MHz if just the sum signal is to be monitored, a single transducer tuned to 1 MHz if just the difference signal is to be monitored, or one of each such tuned transducers if both the sum signal and difference signal are to be monitored. The signal or signals so monitored by transducer block 16 can be passed (along with the amplitudes of the generated compressional waves from generator block 10) to an output device block 18, e.g., display, printer/plotter, etc., where the nonlinear signal(s) can be filtered, processed, monitored and/or stored.

Figure 2:
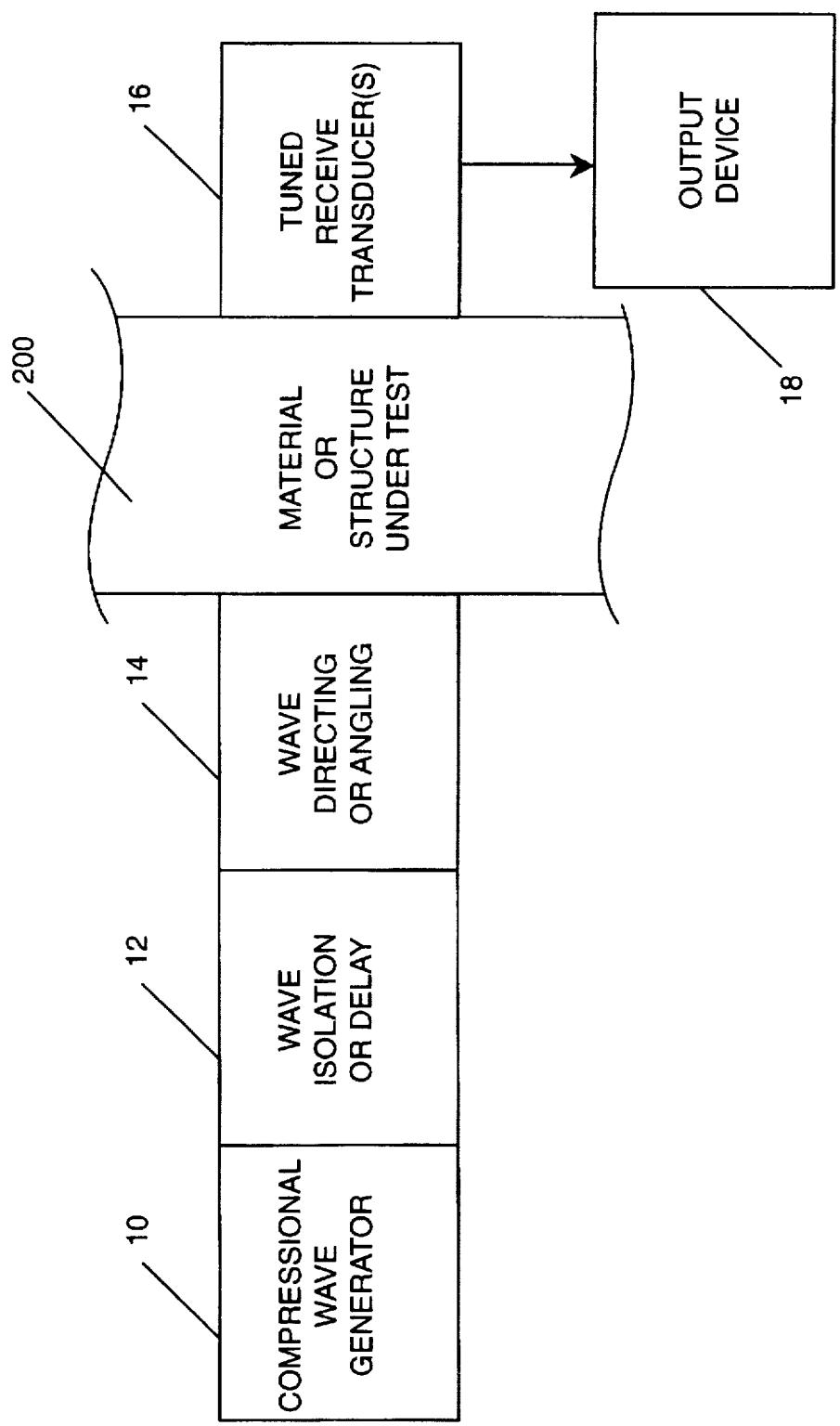
FIG. 2 is a block diagram another embodiment of the scanning system.

An alternative embodiment is depicted in FIG. 2 where like reference numerals are used for those elements common with the embodiment depicted in FIG. 1. In FIG. 2, however, tuned receive transducer(s) 16 are mounted on the side of material 200 that is opposite the side from which the compressed waves are generated. This configuration is suitable for examining newly manufactured parts, sheet materials, etc. where access to both sides of material 200 is easily achieved. The operating principles for the FIG. 2 embodiment are similar to those described above with respect to the FIG. 1 embodiment as will be explained further below.

Figure 3:
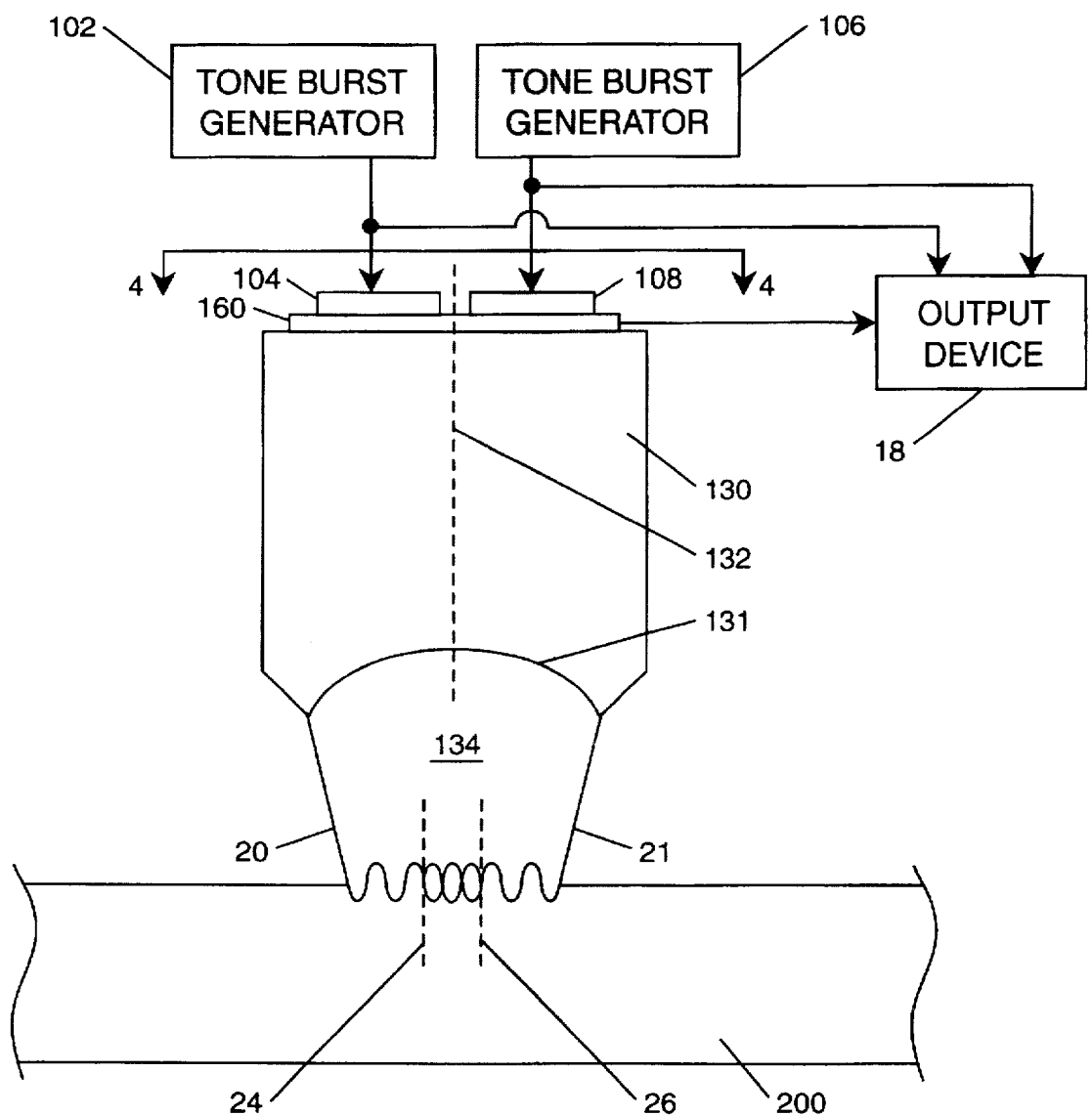
FIG. 3 is a schematic view of one implementation of the preferred embodiment depicted in FIG. 1.
Figure 4:
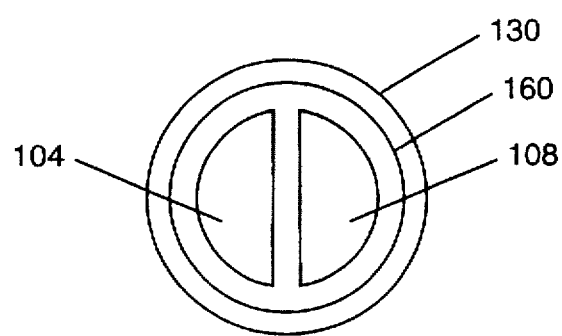
FIG. 4 is a plan view of the scanning system of FIG. 3 taken along line 4—4 depicting an arrangement for the transmission and receiving transducers.

By way of example, one implementation of the configuration of FIG. 1 is shown schematically in FIG. 3. Generator block 10 of FIG. 1 is implemented by tone burst generators 102 and 106 and transducers 104 and 108. In particular, tone burst generator 102/transducer 104 are operated to produce a first compressional wave at a first frequency $f_1$, and tone burst generator 106/transducer 108 are operated to produce a second compressional wave at a second frequency $f_2$. Tuned receive transducer block 16 of FIG. 1 is implemented by a single transducer 160 tuned, for example, to the difference frequency of $(f_1-f_2)$. The wave isolation or delay block 12 and wave directing or angling block 14 of FIG. 1 are implemented by converging acoustic lens 130 which can be made of fused quartz or other similar material with the appropriate ultrasonic and mechanical properties. Such appropriate properties include low attenuation at the operating frequency(ies), low dispersion, material uniformity such that there are minimal material defects, mechanical stability and good machinability.

Lens 130 is of sufficient thickness to serve as an acoustic delay that delays the transmission of the compressional waves during the time tone burst generators 102 and 106 are on. Lens 130 is further shaped at output face 131 to direct the compressional waves produced by transducers 104 and 108. The waves of interest for this embodiment are those emanating from the portions of face 131 furthest from central axis 132 of lens 130. Waves emanating from these portions of face 131 are directed toward one another to form surface waves 20 and 21. Good acoustic coupling between lens 130 and material 200 can be achieved with any suitable fluid coupling medium 134 that transmits compressional waves such as water.

A possible configuration of transducers 104, 108 and 160 is shown in the plane view taken along line 4—4 of FIG. 3. In the illustrated embodiment, each of transducers 104 and 106 are D-shaped mirror images that are separated from one another. In this way, the ultrasonic waves are kept separated until they meet at material 200. Tuned receive transducer 160 is circular and larger than the combination of transducers 104 and 108.

Figure 5:
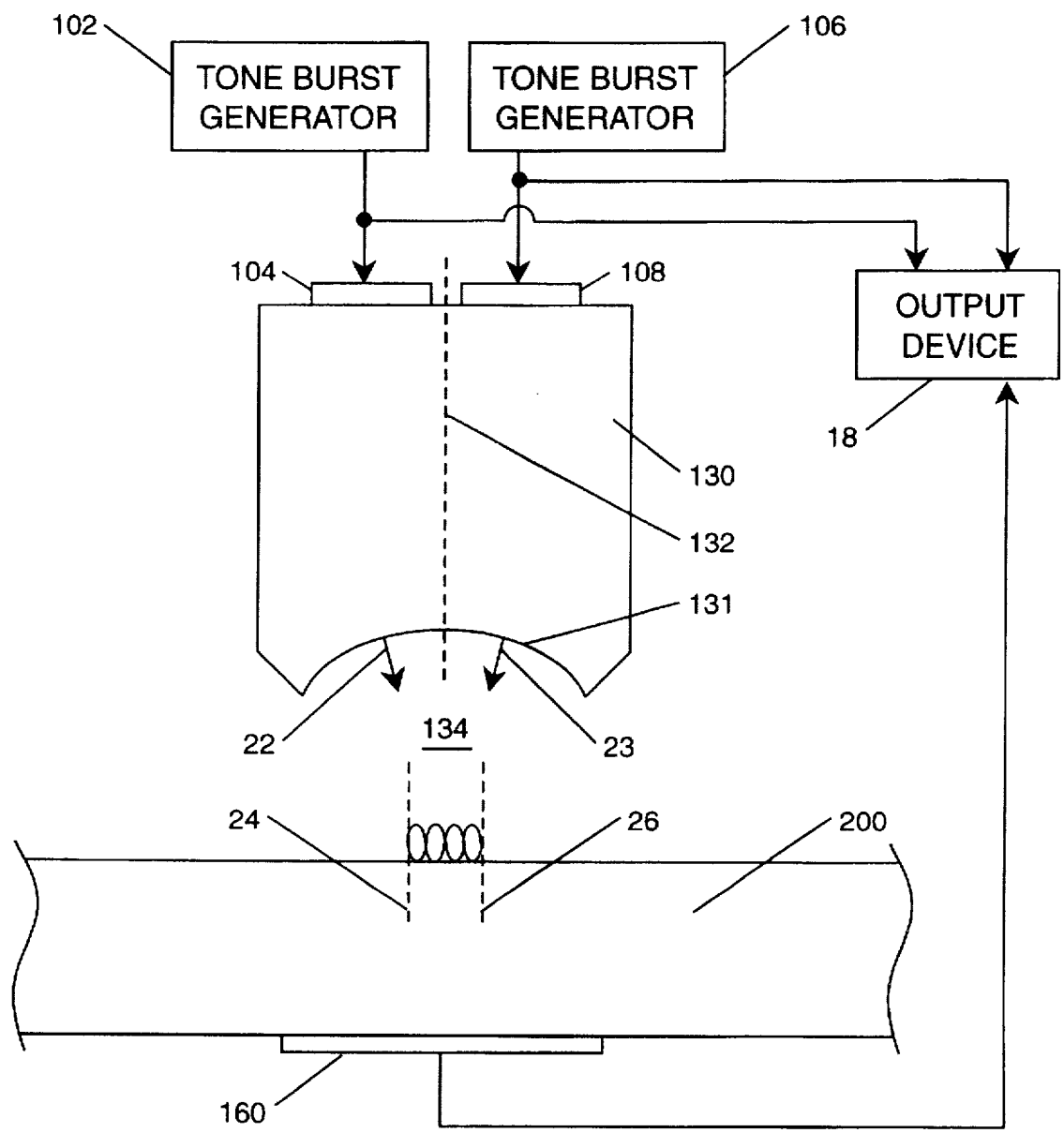
FIG. 5 is a schematic view of one implementation of the alternative embodiment depicted in FIG. 2.

The alternative configuration depicted in FIG. 2 in block form can be realized, for example, by the embodiment depicted in FIG. 5 where like reference numerals are used for those elements common with the embodiment of FIG. 3. In this embodiment, tuned receive transducer 160 is acoustically coupled to the opposite side of material 200 with respect to the source of the compressional waves.

The waves of interest for this embodiment are those emanating from the portions of face 131 nearer to central axis 132 of lens 130. Waves emanating from these portions of face 131 are directed as bulk compressional waves through coupling medium 134. For the purpose of illustration, the bulk compressional waves at frequencies $f_1$ and $f_2$ are represented in FIG. 5 by arrows 22 and 23, respectively. Bulk waves 22 and 23 refract into material 200 and mix at the wave interaction zone between lines 24 and 26. As a result, sum and difference waves are generated as in the FIG. 1 embodiment. However, since the sum and difference waves are generated from bulk compressional waves, the resulting sum and difference waves traverse material 200 after mixing. The sum and/or difference waves can therefore be measured by transducer 160 tuned to either the sum wave's frequency or the difference wave's frequency. Naturally, a second such transducer can be used in order to provide for measurement of both the sum and difference waves. Another embodiment can be realized by combining the embodiments of FIGS. 1 and 2 so that sum and/or difference waves due to mixing of both surface and bulk compressional waves are monitored.

The advantages of the present invention are numerous. The scanning method and system provide a defect detection capability that will allow structures to be repaired or taken out of service before cracks can develop. A structure can be scanned in situ and need not be under stress for accurate measurement. Thus, the present invention is well-suited to be used as part of a preventive maintenance program for a variety of material, vehicle and/or structural applications.

Although the invention has been described relative to a specific embodiment thereof, there are numerous variations and modifications that will be readily apparent to those skilled in the art in light of the above teachings. For example, as mentioned above, the present invention could be carried out using a single frequency wave generator for compressional wave generator block 10 in FIGS. 1 and 2. In such an instance, wave directing or angling block 14 could again be a converging lens causing the propagation of two surface waves of equal frequency f towards one another. The resulting sum wave would thus occur at a frequency of 2f. Note that there would be no difference wave in this example. Other variations of the present invention include the delay aspect which can be implemented acoustically as described herein or electronically according to a method known in the art. Still further, the directing of the compressional waves to form surface waves at the material under test could also be accomplished by passing each transmitted wave through an angled acoustic waveguide block. It is therefore to be understood that, within the scope of the appended claims, the invention may be practiced other than as specifically described.

What is claimed as new and desired to be secured by Letters Patent of the United States is:

1. A method of detecting defects in a material, comprising the steps of:
    mixing waves of a first frequency with waves of a second frequency at an interaction zone in said material to generate at least one of a difference wave and a sum wave in said interaction zone, said difference wave occurring at said first frequency minus said second frequency and said sum wave occurring at said first frequency plus said second frequency;
    measuring the amplitude of at least one of said difference wave and said sum wave; and
    computing a value defined as the amplitude of at least one of said difference wave and said sum wave divided by the product of the amplitude of the waves of said first frequency and the amplitude of the waves of said second frequency, wherein said value is an indication of defects in said interaction zone.

2. A method according to claim 1 wherein said step of mixing comprises the steps of:
    generating a first compressional wave at said first frequency;
    generating a second compressional wave at said second frequency; and
    directing said first compressional wave and said second compressional wave towards one another to mix at said interaction zone.

3. A method according to claim 1 wherein said step of mixing comprises the steps of:
    generating a first compressional wave pulse at said first frequency from a first source;
    generating a second compressional wave pulse at said second frequency from a second source;
    isolating said first compressional wave pulse and said second compressional wave pulse from said first source and said second source during said step of measuring; and
    directing said first compressional wave pulse so isolated and said second compressional wave pulse so isolated towards one another to mix at said interaction zone.

4. A method according to claim 1 wherein said step of measuring includes the step of positioning at least one transducer to detect said at least one of said difference wave and said sum wave radiated from said interaction zone.

5. A method according to claim 1 wherein said first frequency and said second frequency are selected from the ultrasonic frequency range.

6. A method according to claim 1 wherein said step of measuring includes the steps of:
    measuring the amplitude of said difference wave; and
    measuring the amplitude of said sum wave.

7. A method according to claim 1 wherein said first frequency is equal to said second frequency.

8. A system for detecting defects in a material comprising:
    acoustic means for causing waves of a first ultrasonic frequency to mix with waves of a second ultrasonic frequency at an interaction zone in said material such that a difference wave and a sum wave are generated in said interaction zone, said difference wave occurring at said first frequency minus said second frequency and said sum wave occurring at said first frequency plus said second frequency;
    at least one acoustic transducer positioned to detect the amplitude of at least one of said difference wave and said sum wave; and
    means coupled to said acoustic means and said at least one acoustic transducer for determining a product of the amplitude of said waves of said first ultrasonic frequency and the amplitude of said waves of said second ultrasonic frequency and for monitoring the amplitude of a nonlinear signal defined as the amplitude of one of said difference wave and said sum wave relative to said product of the amplitude of said waves of said first ultrasonic frequency and the amplitude of said waves of said second ultrasonic frequency, wherein the amplitude of said nonlinear signal is an indication of defects in said interaction zone.

9. A system as in claim 8 wherein said acoustic means comprises:
    acoustic signal generator means for generating a first compressional wave at said first ultrasonic frequency and for generating a second compressional wave at said second ultrasonic frequency;
    acoustic wave guide means coupled to said acoustic generation means for directing said first compressional wave and said second compressional wave towards one another to mix at said interaction zone; and
    a fluid medium acoustically coupling said acoustic wave guide means to said material.

10. A system as in claim 9 wherein said acoustic wave guide means is a converging acoustic lens.

11. A system as in claim 9 wherein said fluid medium is water.

12. A system as in claim 8 wherein said acoustic means comprises:
    acoustic signal generator means for generating a first compressional wave pulse at said first ultrasonic frequency and for generating a second compressional wave pulse at said second ultrasonic frequency;

isolation means coupled to said acoustic signal generator means for isolating said first compressional wave pulse and said second compressional wave pulse from said acoustic signal generator;

an acoustic lens coupled to said isolation means for directing said first compressional wave pulse so isolated and said second compressional wave pulse so isolated towards one another to mix at said interaction zone; and a fluid medium acoustically coupling said acoustic lens to said material.

13. A system as in claim 12 wherein said acoustic lens is a converging acoustic lens.

14. A system as in claim 12 wherein said fluid medium is water.

15. A system as in claim 8 wherein said acoustic means comprises:

acoustic signal generator means for generating a first compressional wave pulse at said first ultrasonic frequency and for generating a second compressional wave pulse at said second ultrasonic frequency;

a converging acoustic lens coupled to said acoustic signal generator means for delaying propagation of said first compressional wave pulse and said second compressional wave pulse therefrom until said acoustic signal generator has completed generation of said first compressional wave pulse and said second compressional wave pulse, said converging acoustic lens further directing said first compressional wave pulse and said second compressional wave pulse towards one another to mix at said interaction zone; and a fluid medium acoustically coupling said converging acoustic lens to said material.

16. A system as in claim 15 wherein said fluid medium is water.

17. A system as in claim 8 wherein said first ultrasonic frequency is equal to said second ultrasonic frequency.

18. A method according to claim 1 further comprising the step of holding constant the amplitude of said waves of said first frequency and the amplitude of said waves of said second frequency.

19. A method according to claim 1 further comprising the step of scanning said waves of said first frequency and said waves of said second frequency across the material, wherein said interaction zone is thereby scanned across the material.

20. A method of detecting dislocation dipoles in a material, comprising the steps of:

mixing fixed amplitude waves of a first frequency with fixed amplitude waves of a second frequency at an interaction zone in said material to generate at least one of a difference wave and a sum wave in said interaction zone, said difference wave occurring at said first frequency minus said second frequency and said sum wave occurring at said first frequency plus said second frequency; and measuring the amplitude of at least one of said difference wave and said sum wave as an indication of dislocation dipoles in said interaction zone.

* * * * *